United States Patent [19]

Masamune et al.

[11] Patent Number: 5,298,623
[45] Date of Patent: Mar. 29, 1994

[54] CU COMPLEXES OF BIS-OXAZOLINES AND THEIR USE

[75] Inventors: Satoru Masamune, Newton; Richard E. Lowenthal, Waltham, both of Mass.

[73] Assignee: Massachusetts Institute of Technology, Cambridge, Mass.

[21] Appl. No.: 789,748

[22] Filed: Nov. 8, 1991

[51] Int. Cl.$^5$ ............................................. C07D 233/20
[52] U.S. Cl. ....................................... 548/101; 548/108
[58] Field of Search ................ 548/101, 108; 514/183, 514/184

[56] References Cited

PUBLICATIONS

Lowenthall et al, Tetrahedron Letters vol. 31 No. 42 pp. 6005-6008 (Oct. 1990).

*Primary Examiner*—Nicholas S. Rizzo
*Attorney, Agent, or Firm*—Buchanan Ingersoll

[57] ABSTRACT

This invention describes Cu complexes of bis-oxazolines and their use. These compounds have the following formulas:

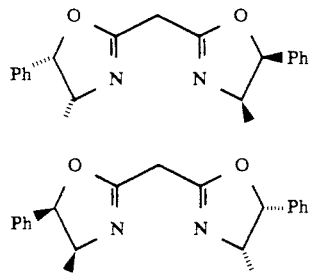

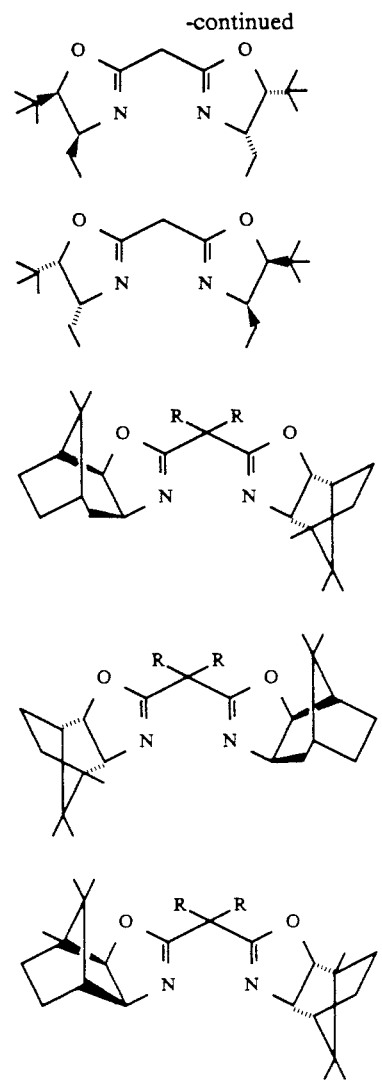

(Abstract continued on next page.)

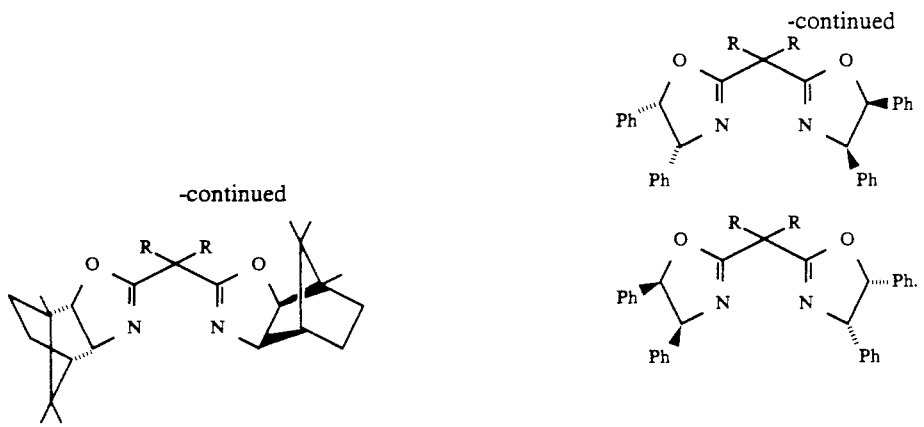
12 Claims, No Drawings

CU COMPLEXES OF BIS-OXAZOLINES AND THEIR USE

INTRODUCTION

This project is supported in part by N. I. H. grant GM-35879.

BACKGROUND OF THE INVENTION

Pyrethroids are useful as insecticides. Among the proprietary pyrethroids there may be mentioned for example fenvalerate which has wide application in agricultural fields. These compounds are further characterized as having high activity against insects and low mammalian toxicity.

Chemically, these compounds can be readily prepared from (+)-trans-chrysanthemic acid, i.e. 2,2-dimethyl-3-(2-methylpropenyl)-cyclopropanecarboxylic acid. It has been found that there is a close correlation between the chirality of this molecule and its insecticide activity. Among the four optical isomers of chrysanthemic acid exhibiting insecticidal activity, the most effective isomer is found to be the (+)-trans isomer. The next most effective isomer is the corresponding (+)-cis isomer. In contrast, the (−)-trans and the (−)-cis isomers are almost ineffective as insecticides. On the other hand, the naturally occurring chrysanthemic acid has the (+) (1R)-trans configuration.

The present invention relates to Cu complexes of new bis-oxazolines useful in the catalytic cyclopropanation of trisubstituted and unsymmetrical cis-1,2-disubstituted olefins exhibiting high enantoselectivity. The resulting cyclopropanated products are useful in the production of the desired pyrethroids and their derivatives.

DESCRIPTION OF THE PRIOR ART

Lowenthal et al., *Tetrahedron Letters*, Vol. 31, No. 42, pp 6005–6008, 1990 and references cited therein teach bis-oxazolines of the formulas:

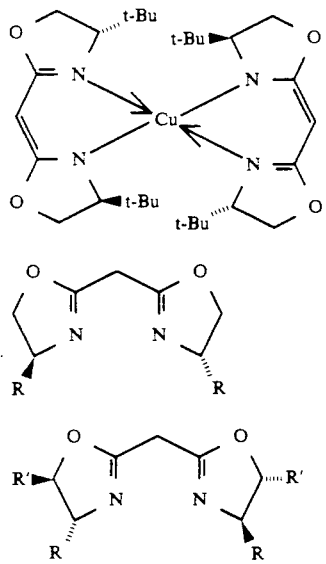

Arantani, T. describes in the paper *Pure & Appl. Chem.* Vol. 57, No. 12, pp. 1639–1644, 1985, the asymmetric catalytic cyclopropanation to form pyrethroids. In this process, he uses copper and diazoacetate esters to prepare cyclopropanecarboxylic acids. The best product ratio described in this paper using 1-menthyl diazoacetate is 93% trans: 7% cis.

The paper also describes as catalysts chiral Schiff based-copper complexes.

The Bolm paper in *Angew. Chem.* 1991, 103, 556, is a review article relating to bis-oxazolines.

Evans et al. in *J. Am. Chem. Soc.* 1991, 113, 726 describes the chemistry which was disclosed in the aforementioned *Tetrahedron Letters*. It also describes a different ligand and the use of copper triflate.

In the Corey et al. paper, *J. Am. Chem Soc.* 1991, 113, 728, use of a certain chiral ligand in a Diels-Alder reaction using iron as the metallic catalyst.

The Pfaltz paper in *Helvetica Chimica Acta* 1991, 74, 232, describes the chemistry substantially similar as disclosed in the aforementioned *Tetrahedron Letters*.

The Helmchen paper published in *Synlett*, 1991, 257 describes the use of the ligand designed for the hydrosilylation of acetophenones.

The Lehn et al. paper in *Helvetica Chimica Acta* 1991, 74, 1, it describes the synthesis of copper II complexation and the X-ray analysis of the bis-oxazoline ligand.

Finally, the Doyle et al. paper published in *J. Am. Chem. Soc.* 1991, 112, 1906 discloses the use of rhodium catalysts such as rhodium carboxylate and carboxylamide for the cyclopropanation of olefins with diazoacetates such as 2,6-di-tert-butyl-4-methylphenyl diazoacetate yielding products which are in the racemic form. The authors try to improve the trans/cis ratio by changing the alcoholic group of the diazoacetate.

SUMMARY OF THE INVENTION

The present invention relates to copper I complexes of bis-oxazolines, the structural formulas of which are more fully described below.

These compounds are prepared from the corresponding amino alcohols and malono-bis-imidate. In the catalytic cyclopropanation of trisubstituted and unsymmetrical cis-1,2-disubstituted olefins, these compounds influence and exhibit high enantioselectivity of up to 95%ee.

The present invention also includes within its scope new and novel reactions involving the complexes with diazoacetate giving pyrethroids having high trans/cis ratios of up to 99:1 trans.

As mentioned above, pyrethroids such as fenvalerate are important compounds useful in the agricultural field. Chemically, these compounds have in common the configuration corresponding to the trans-chrysanthemate configuration. Accordingly, the present invention provides new and important copper complexes of these oxazolines useful for the cyclopropanation of certain olefins yielding intermediates particularly suitable for the production of the isomer particularly suitable for the conversion into pyrethroids.

DETAILED DESCRIPTION OF THE INVENTION

According to the present invention, we provide Cu complexes (Cu . $X_n$) of bis-oxazolines having the following structural formulas:

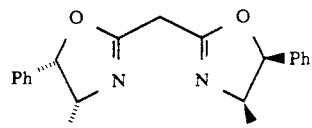

-continued

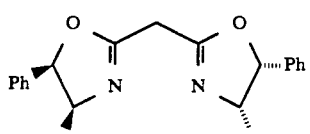

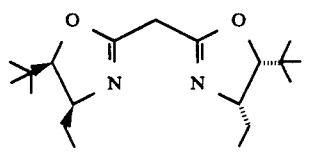

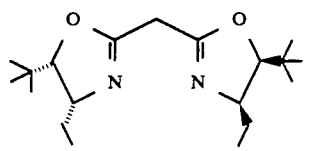

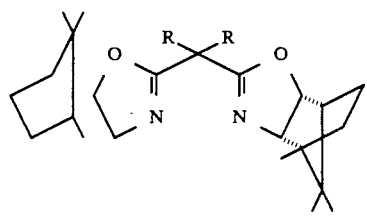

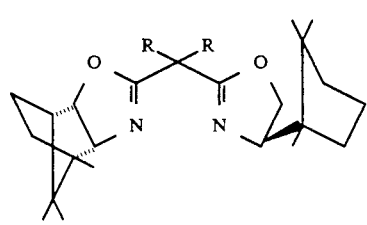

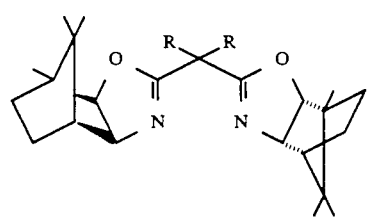

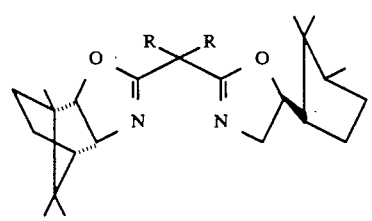

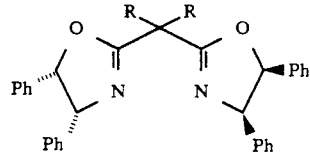

-continued

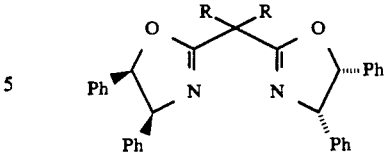

In the above structural formulas, R is hydrogen or methyl, Ph is phenyl or substituted phenyl and n is 1 or 2 and Cu is CuOTf, CuO-t-Bu, $CuClO_4(CH_3CN)_2$ or Cu (II) followed by activation, e.g. reduction, with the provision that when n is 1 Cu(II) is selected from Cu-$(OTf)_2$, $Cu(OtBu)_2$ or $Cu(ClO_4)_2$.

In the above definition for "substituted phenyl", it is meant to be a mono-, di- or trisubstituted phenyl in which the substituents, which may be equal or different, is selected from $C_1$-$C_6$ alkyl, $C_1$-$C_6$ alkoxy, halo or amino. Among the $C_1$-$C_6$ alkyl, there may be mentioned, for example, methyl ethyl, propyl and the like. Similarly, $C_1$ to $C_6$ alkoxy there maybe mentioned, for example, methoxy, ethoxy, propoxy and the like. Cu(II) may be readily prepared from known procedures, e.g. according to the description in the aforementioned Lowenthal et al. reference.

According to the first step of the present invention, the Cu complexes of the ligands described in the foregoing formulas are prepared. Thus, in a typical process, the selected starting amino alcohol, e.g. (+)-2-amino-1,2-diphenyl ethanol is combined with malono-bis-imidate in a dry inert atmosphere such as argon using an anhydrous solvent such as a halogenated solvent. Typically, the reaction is effected at ice water temperature, e.g. between about −5° C. to about 5° C. and preferably at 0° C. The desired reaction product is recovered from the mixture using standard procedures.

The catalytic cyclopropanations thereafter are carried out in a standard fashion. For example, the catalyst is prepared with copper triflate CuOTf and a selected ligand as described above. Among the copper sources, we have found that a Cu(II) complex or the Cu triflate complex with the selected ligand offers excellent diastereoselectivity (trans:cis) and enantoselectivity u to 95%ee of the pyrethroids. These catalytic cyclopropanations using these complexes of the present invention are applicable to trisubstituted, unsymmetric cis-1,2-disubstituted olefins as well as terminally blocked olefins. Among the halogenated solvents, there may be mentioned, for example, methylene chloride, chloroform, 1,2-dichloromethane and the like.

As an illustration, the foregoing reaction can be represented by the following reaction scheme

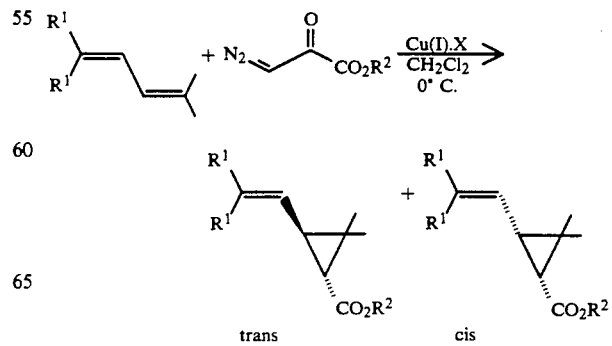

trans      cis where X is

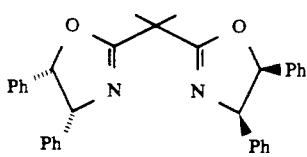

and Cu . $X_n$ is employed at about 0.1 mole % to about 1 mol %, usually at about 1 mole %.

The foregoing process represents a distinct improvement over the process described in Arantani cited above. Thus using our process, we obtain a product ratio of 97% trans: 3% cis of chrysanthemate esters The procedure to obtain pyrethroid is well known Please see the procedure described in the aforementioned Arantani paper and the references disclosed therein.

In order to further illustrate the practice of this invention, the following examples are included.

EXAMPLES

A Ligand Synthesis

1. General Procedure For R=H

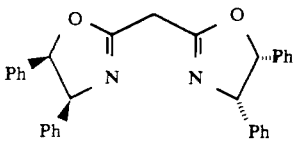

In a clean, dry 500 ml flask, 8 grams (37.56 mmol) (+)-2- amino-1, 2-diphenylethanol was combined with malo-bis-imidate (4.33 g; 18.75 mmol) under argon and 400 ml $CH_2Cl_2$ was added at 0° C. To this suspension was added triethylamine (10.45 ml; 95.12 mmol) and the mixture was stirred for 24 hours at 23° C. The solvent was evaporated and vacuum dried for 30 minutes to remove excess triethylamine. The residue was dissolved in $CH_2Cl_2$ and purified by column chromatography on 400 grams neutral alumina gel, eluting with 2 liters 2% MeOH/1% $NH_3/CH_2Cl_2$. The pure fractions were combined and concentrated. Recrystallization from $CH_2Cl_2$/hexane provides 6.18 grams (72% yield) (+) 4,4', 5,5'-bis-(cisdiphenyloxazolylmethane.

Data $^1$H NMR (CDCl$_3$): δ 3.91(s, 2H, CH$_2$); 5.66 (d, 2H, J=10.2 Hz, CH); 5.99 (d, 2H, J=9.9 Hz, CH); 7.01 (d, 20H, J=8.4 Hz, Ph).

$^{13}$C NMR (CDCl$_3$): δ 29.06 (CH$_2$); 74.09 (CH); 86.13 (CH); 126.9, 126.52, 126.52, 126.86, 127.33, 127.38, 127.53, 127.58, 127.63, 127.7, 127.81(arom CH); 136.03, 137.34 (arom C); 163.08(C).

IR (CHCl$_3$): 1660s, 1490m, 1470m, 1455m, 1385m, 1360m, 990s, 700m.

HRMs: 458.19941 (m+), 180(100), 458.3(5.51).

$[α]_D^{25}$= −240°(CH$_2$Cl$_2$, c=2.00).

m.p.=199°-200° C.

The enantiomer has the following chemistry

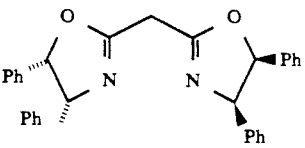

$[α]_D^{25}$= +240.5°(CH$_2$Cl$_2$, c=2.10).

m.p.=199°-200° C.

2. General Procedure For R=CH$_3$

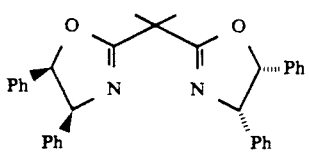

The (+)-2-amino-1,2-cis-diphenylethanol (2 g; 9.39 mmol) was placed in a clean dry flask under argon and 35 ml CH$_2$Cl$_2$ was added. The solution was cooled to 0° C. and (2.6 ml, 18.8 mmol) NEt$_3$ was added. To this solution was added 790 mg (4.7 moles) dimethyl malono-bis-acid chloride dropwise. The mixture was stirred for 8 hours and poured into saturated aqueous NH$_4$Cl. Extraction with 3 portions CH$_2$Cl$_2$ (25 ml), followed by concentration and crystallization from CH$_2$Cl$_2$ gave 4.8 grams (98%) bis-amide (m.p. 180°-182° C.).

The crude bis-amide (4.8 g; 9.3 mmol) was suspended in 200 ml xylene and heated to reflux with a dean stark trap for 3 hours. The reaction was briefly cooled below boiling and 136 mg (0.45 mmol) dibutyl tin dichloride was added. The mixture was refluxed for 48 hours. After evaporation, the residue was taken up to CH$_2$Cl$_2$ and column chromatographed on 150 grams neutral alumina eluting with 3%MeOH/1%NH$_3$/CH$_2$Cl$_2$. Chrystallization from CH$_2$Cl$_2$/hexane provides 3.7 grams (82%) bis-oxazoline.

Data $^1$H NMR (CDCl$_3$): δ 1.98 (s, 6H, CH$_3$); 5.65 (d, 2H, J=10.8 Hz, CH); 6.02 (d, 2H, J=9.9 Hz, CH); 7.04 (d, 20H, J=16.2 Hz, Ph).

$^{13}$C (CDCl$_3$): δ 24.85 (CH$_3$); 39.55 (CH$_2$); 73.89 (CH); 86.34 (CH); 126.60, 126.97, 127.42, 127.66, 127.91, (arom CH); 136.34, 137.58 (arom C): 170.40 (C).

IR (CHCl$_3$): 1665s, 1480m, 1470m, 1455m, 1390m, 1370, 995s, 705m. $[α]^{D25}$= −365° (CH$_2$Cl$_2$, c=1.15).

m.p.=154°-155° C.

The enantiomer has the following chemistry

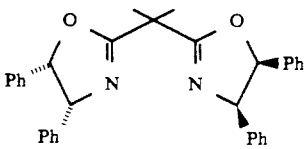

$[α]_D^{25}$= +367° (CH$_2$Cl$_2$, c=1.05).

m.p.=155°-156° C.

a.) The following compound was prepared in a similar manner.

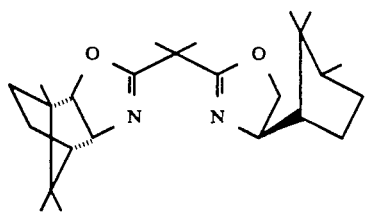

Data

¹H NMR (CDCl₃): δ 0.808 (s, 6H, CH₃); 0.86 (m, 6H, CH₃); 0.87 (m, 4H, CH₂); 0.99 (s, 6H, CH₃); 1.45 (dt, 4H, J=2.7 Hz, CH₂); 1.66 (m, 4H, CH₂); 2.09 (d, 2H J=2.4 Hz, CH); 3.09 (s, 2H, CH₂); 3.83 (d, 2H, J=6.6 Hz, CH); 4.45 (d, 2H, J=8.4 Hz, CH).

¹³C NMR (CDCl₂): δ 18.54(CH₃); 22.73 (CH₃); 23.21 (CH₃); 32.65 (CH₂); 34.13 (C); 46.47 (CH₂); 48.29 (CH); 48.75 (C); 72.05 (CH); 88.00 (CH); 170.6 (C).

IR (CHCl₃): 1660s, 1490m, 1470m, 1455m, 1385m, 1360m, 990s, 700m

HRMs: 370.2618 (m+), 95(100), 370.4(25.92), 371.4(7.51)

$[\alpha]_D^{25} = +245°$ (CH₂Cl₂, c=1.12).

Yield: 65%; m.p. =294°-295° C.

b.) The following compound was prepared in a similar manner.

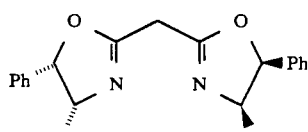

Data

¹H NMR (CDCl₃): δ 1.36 (d, 6H, J=7.5 Hz, CH₃); 3.51 (s, 2H, CH₂); 4.02 (q, 2H, J=6.2 Hz, CH); 4.95 (d, 2H, J=8 Hz, CH); 7.29 (s, 10H, Ph).

IR (CDCl₂): 1670s, 1495m, 1475m, 1460m, 1380m, 1360m, 990s, 705m.

$[\alpha]_D^{25} = +125°$ (CH₂Cl₂, c=125).

HRMs: 334.1679 (m+), 118(100), 334.2(10.6).

Yield: 78%; b.p. 85°-90° C. (0.01 torr).

c.) The following compound was prepared in a similar manner.

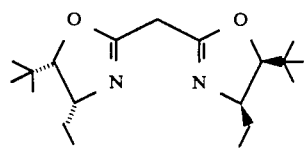

Data

¹H NMR (CDCl₃): δ 1.31 (s, 18H, (CH₃)₃); 1.37 (+, 6H, CH₃); 2.10 (m, 2H, CH₂); 2.25 (m, 2H, CH₂); 3.55 (s, 2H, CH₂); 3.85 (d, 2H, J=6.6 Hz, CH); 4.20 (d, 2H, J=8 Hz, CH).

IR: 1675s, 1490m, 1475m, 1380m, 1360m, 990s, 700m.

$[\alpha]_D^{25} = +114°$ (c=1.1, CH₂Cl₂).

Yield: 68%; b.p. 80°-85° C. (0.01 torr).

d.) The following compound was prepared in a similar manner.

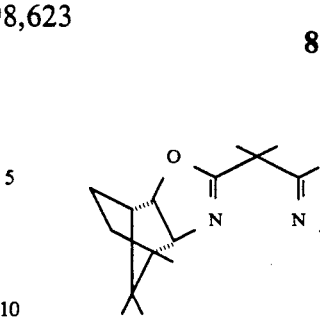

Data

¹H NMR (CDCl₃): δ 0.85 (s, 6H, CH₃); 0.91(s, 6H, CH₃); 0.89 (m, 4H, CH₂); 0.99 (s, 6H, CH₃); 1.48 (quin, 4H, J=4 Hz, CH₂); 1.7 (m, 2H, CH₂); 2.05 (d, 2H, J=2.5 Hz, CH); 3.08 (s, 2H, CH₂); 4.00 (d, 2H, J=6.7 Hz); 4.28 (d, 2H, J=8 Hz, CH).

IR (CHCl₃): 1665s, 1490m, 1475m, 1455m, 1385m, 1360m, 990s, 700m.

HRMs: 370.2618 (m+), 95(100), 370.4(6.38), 371.3(4.58).

$[\alpha]_D^{25} = +185°$ (c=1.1, CH₂Cl₂).

Yield: 70%; m.p. 87°-90° C.

e.) The following compounds was prepared in a similar manner.

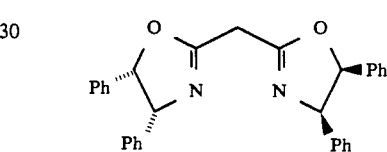

Data: Same as a. above.

$[\alpha]_D^{25} = +240.5°$ (c=2.10, CH₂Cl₂).

m.p.=199°-200° C.

f.) The following compound was prepared in a similar manner.

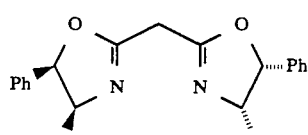

Data $[\alpha]_d^{25} = -125°$ (c=1.25, CH₂Cl₂),

Yield 75%; b.p. 110°-115° C. (0.01 torr).

g.) The following compound was prepared in a similar manner.

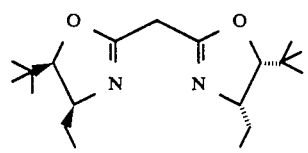

Data

Yield 65%; b.p. 88°-95° C. (0.01 torr).

h.) The following compound was prepared in a similar manner.

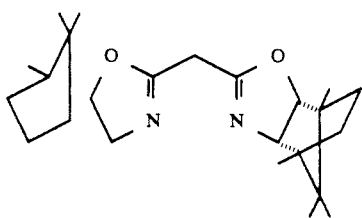

Data

[α]$_D^{25}$ = 248° (c = 1.15, CH$_2$Cl$_2$).
m.p. 292°–294° C.

i.) The following compound was prepared in a similar manner.

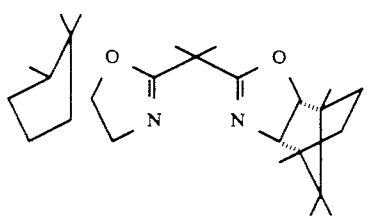

Data

[α]$_D^{25}$ = −182° (c = 1.15, CH$_2$Cl$_2$).
m.p. 88°–91° C.

j.) The following compound was prepared in a similar manner.

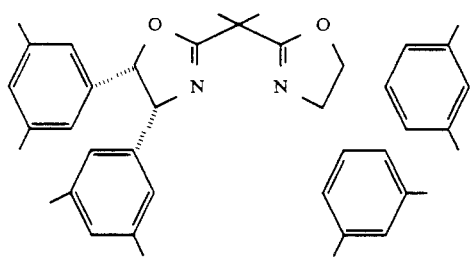

Data m.p. = 185°–187° C.

k.) The following compound was prepared in a similar manner.

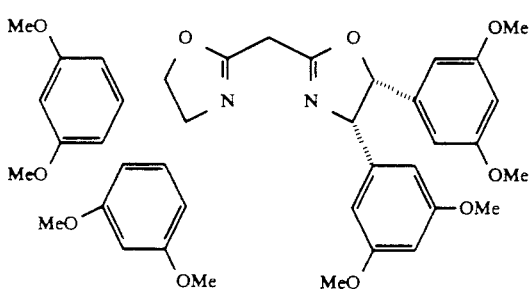

l.) The following compound was prepared in a similar manner.

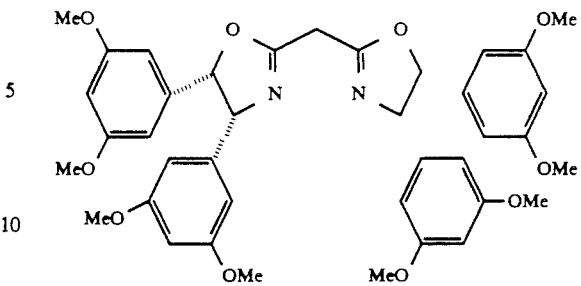

m.) The following compound was prepared in a similar manner.

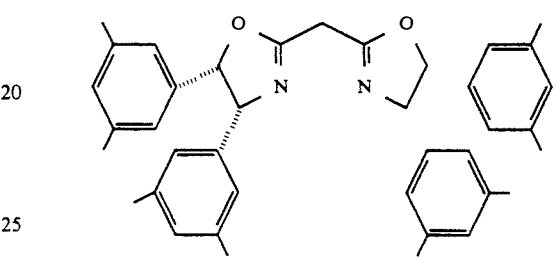

n.) The following compound was prepared in a similar manner.

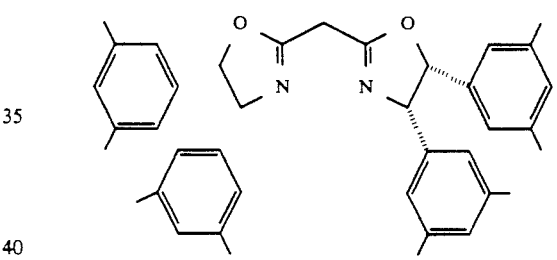

B. Synthesis Of (+)-trans-Chrysanthemic Acid

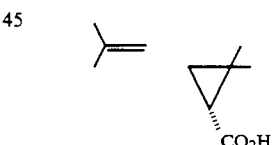

1. Using CuOTf

The CuOTf benzene complex (11.3 mg; 0.055 mmol) was weighed out under nitrogen into a clean dry 25 ml flask and 2.5 ml CH$_2$Cl$_2$ was added. To this was added dropwise (+)-4,4',5,5'-bis-(cis diphenyloxazolyl)dimethylmethane in 2.5 ml CH$_2$Cl$_2$ and the mixture was stirred for 1 hour. This solution was filtered via cannula into a 50 ml reaction vessel containing 2,5-dimethyl-2,4-hexadiene (7.75 ml; 55 mmol) in 15 ml CH$_2$Cl$_2$ under argon. A solution of dicyclohexylmethl (DCM) diazoacetate (1.45 g; 5.5 mmol) in 5 ml CH$_2$Cl$_2$ was added dropwise by syringe pump over a 2 hour period at 0° C. The mixture was allowed to warm to 23° C. and stirred an additional 12 hours. Filtration through 5 grams of silica gel followed by evaporation provided a pale yellow residue. Bulb-to-bulb transfer at 0.1 torr provided 1.62 g (84%) chrysanthemate ester.

2. Using Cu(II)

The copper-ligand complex prepared as described in Lowenthal et al., *Tetrahedron Letters*, Vol. 31, No. 42, 1990, (48.9 mg; 0.05 mmol) was placed in a dry 25 ml flask under argon and dissolved in 15 ml $CH_2Cl_2$. To this was added 2,5-dimethyl-2,4-hexadiene (7.75 ml; 55 mmol) followed by activation with phenylhydrazine (0.05 ml; 0.05 mmol). The mixture was stirred 15 minutes and rapidly went from dark purple to pale yellow. A solution of (1.45 g, 5.5 mmole) DCM diazoacetate in 5 ml $CH_2Cl_2$ was added dropwise over a 2 hour period at 0° C. The mixture was stirred an additional 12 hours, filtered through 5 grams silica gel with 10% EtOAc in hexane and concentrated. Bulb-to-bulb distillation provided chrysanthemate ester 1.60 grams (84%).

3 Using $CuClO_4(CH_3CN)_4$

The $CuClO_4(CH_3CN)_4$ (17.9 mg; 0.055 mmol) was weighed out into a 25 ml round bottom flask and vacuum dried for 1 hour, periodically warming with a heatgun to dry. After added dropwise to give a colorless solution which, after 30 minutes, was filtered into a 50 ml flask containing 2,5-dimethyl-2,4-hexadiene (7.75 ml; 55 mmol) in 5 ml $CH_2Cl_2$ under argon. A solution of DCM diazoacetate (1.45 g; 5.5 mmol) in 5 ml $CH_2Cl_2$ was added dropwise by syringe pump over a 2 hour period (this solution was often prefiltered through dry alumina to ensure removal of $H_2O$) at 0° C. The mixture was allowed to warm slowly to 23° C. and stirred an additional 12 hours. The green mixture was filtered with 10% EtOAc/hexane through a short path chromatography column containing 5 grams of silica gel to remove the catalyst. Evaporation of solvent and excess olefin provided a pale yellow residue which was purified by bulb-to-bulb distillation (0.05 torr) to provide the produce as a white solid, 1.48 grams (78%).

4. Hydrolysis To Chrysanthemic Acid

The chrysanthemate ester (1.64 grams) was dissolved in 80 ml ethanol and 5 ml $H_2O$. To this was added 0.5 gram NaOH and the mixture was refluxed for 48 hours. The solution was concentrated to 5 ml and 30 ml $H_2O$ was added. The aqueous layer was extracted 2×with 10% EtoAc in hexane to remove dicyclohexylmethanol. Adjustment of pH to 4 with HCl and extraction with 3 portions of EtOAc provides chrysanthemic acid (716 mg; 90%) (>150:1 trans:cis ratio; 95%ee).

Data $^1$H NMR (CDCl$_3$) δ 1.16 (s, 3H, CH$_3$); 1.32 (s, 3H, CH$_3$); 1.40 (d, 1H, J=5 Hz, CH); 1.72 (s, 6H, CH$_3$); 2.12 (t, 1H, J=5.5 Hz); 4.91(d, 1H, J=7.8 Hz, CH); 12.1 (bs, 1H, CO$_2$H).
IR (CHCl$_3$): 3610 bs, 2660m, 1670m.
$[\alpha]_{D25}= +25.46°$ (c=1.15, CHCl$_3$).
$[\alpha]_D^{25}= +14.1°$ (c=1.5, EtOH).
m.p.=20°-21° C.

C. Synthesis Of (+)-trans-Permenthric Acid

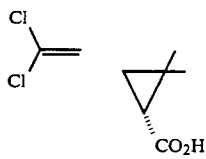

1. Procedure is identical to that for B.2.) using 0.05 mmol of the copper-ligand catalyst (1.45 g), 5.5 mmol DCM diazoacetate and 8.2 ml 1,1-dichloro-4-methyl-1,3-pentadiene one obtains 1.2 g (62%) of permenthric ester.

2. Hydrolysis under conditions described in B.4.) gives 0.589 g (91%) pure (+)-trans-permenthric acid.

Data $^1$H NMR (CDCl$_3$): δ=1.18 (s, 3H, CH$_3$); 1.27 (s, 3H, CH$_3$); 1.54 (d, 1H, J=5.5 Hz, CH); 2.22 (dd, 1H, J=3.2 Hz, CH); 5.58 (d, 1H, J=8 Hz, CH).
IR (CHCl$_3$): 3620bs, 2550m, 1690m.
$[\alpha]_D^{25}= +27.95$ (c=1.10, CHCl$_3$).
m.p.=37°-39° C.

D. Synthesis of Cyclohexylmethyl diazoacetate (DCM diazoacetate)

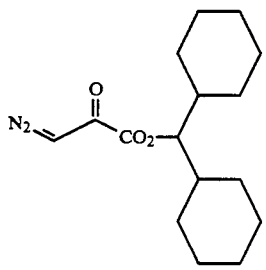

1. To a solution of dicyclohexylmethanol (25g; 127.6 mmol) in 200 ml Et$_2$O was added NEt$_3$ (35.5 ml; 255 mmol) and cool to 0° C. Chloroacetyl chloride (14.4 g; 130 mmol) was added dropwise and stirred 8 hours at 23° C. Pour into NaHCO$_3$ (sat) (200 ml) and extract with Et$_2$O. Dry with MgSO$_4$ and filter through Celite. Evaporation provides 32.5 grams (94%) crude ester.

2. The crude dicyclohexylmethyl ester was dissolved in 200 ml DMF and 100 ml saturated NH$_4$OH was added. Warm to 60° C. and stir 24 hours. Pour into H$_2$O and extract with 400 ml EtOAc. Wash 3×with 100 ml portions of H$_2$O. Dry organic layer over MgSO$_4$ and filter. Concentration provides 26.54 g (78%) of crude amine.

3. The crude amine (26.54 g; 105.7 mmol) was dissolved in 400 ml and (14.625 g; 125 mmol) isoamyl nitrate was added followed by 12.5 ml AcOH. The mixture was heated to reflux for 6 hours. The solution was concentrated to approximately 50 ml and purified by column chromatography in five 10 ml portions. The combined pure fractions were concentrated and recrystallized in hexane to give 17.9 g (65%) dicyclohexylmethyl diazoacetate.

Data $^1$H NMR (CDCl$_3$): δ 1.01 (m, 5H, CH$_2$); 1.15 (m, 5H, CH$_2$); 1.65 (m, 11H, CH/CH$_2$); 4.68 (t, 1H, J=5.5 Hz, CH); 4.72 (s, 1H, CH).
$^{13}$C NMR (CDCl$_3$): δ 26.078, 26.26, 26.40, 27.44, 29.92 (CH$_2$); 38.53 (CH); 45.81 (CH); 82.02 (CH); 16.71 (C).
IR (CHCl$_3$): 2105m, 1694s.
m.p.=75°-76° C.

What is claimed is:

1. A compound of the formula $$Cu.X_n$$

wherein X is a member selected from ligands of the formula

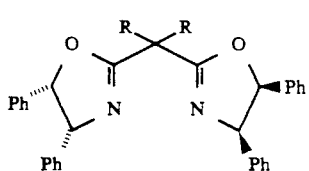

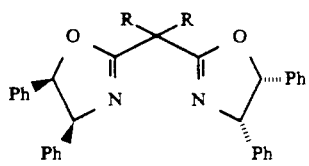

wherein R is hydrogen or methyl, Ph is phenyl or substituted phenyl, n is 1 or 2 and Cu is CuOTf, CuO-t-Bu, CuClO$_4$(CH$_3$CN)$_2$ or Cu(II) followed by activation with the provision that when n is 1 Cu(II) is selected from Cu(OTf)$_2$, Cu(OtBu)$_2$ or Cu(ClO$_4$)$_2$.

2. A compound according to claim 1 in which X is

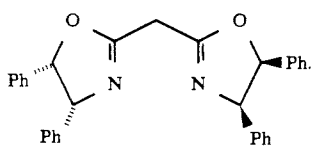

3. A compound according to claim 1 in which X is

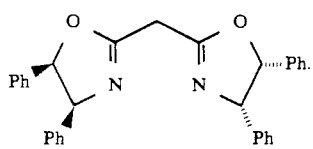

4. A compound according to claim 1 in which X is

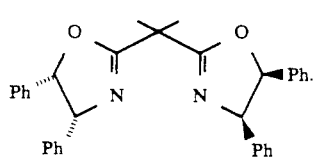

5. A compound according to claim 1 in which X is

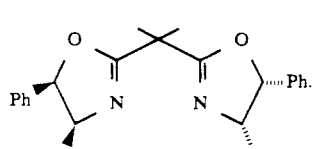

6. A compound according to claim 1 in which X is

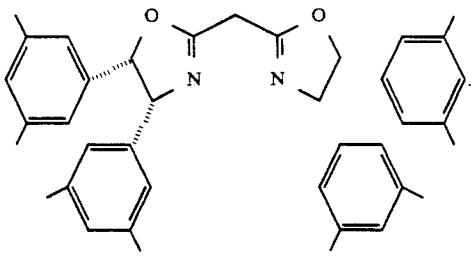

7. A compound according to claim 1 in which X is

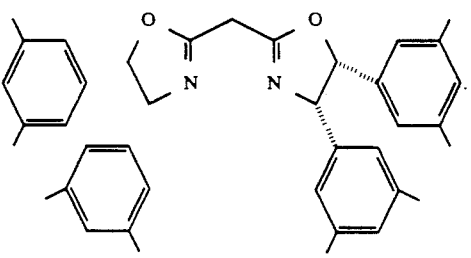

8. A compound according to claim 1 in which X is

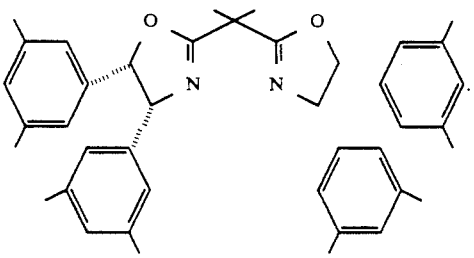

9. A compound according to claim 1 in which X is

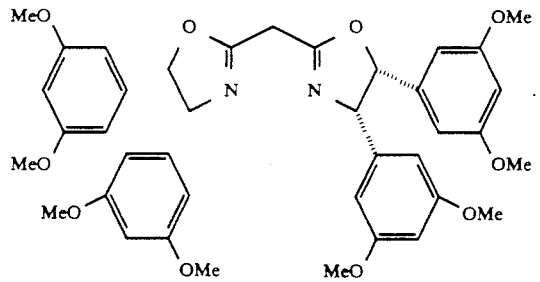

10. A compound according to claim 1 in which X is

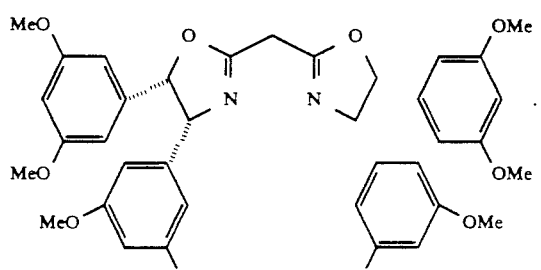

11. A compound according to claim 1 in which X is
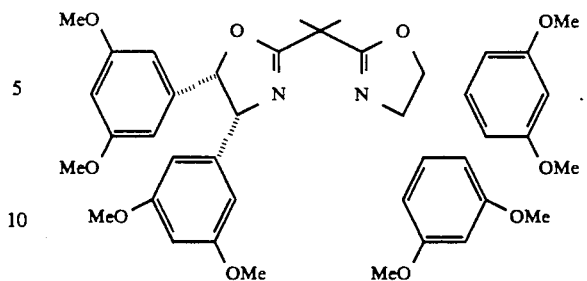
12. A compound of the formula
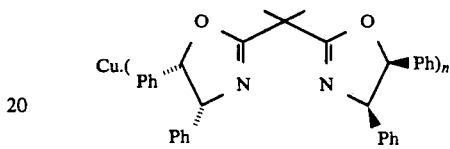
in which Ph and n are as defined in claim 1.
* * * * *